United States Patent [19]

Bay

[11] 4,333,180
[45] Jun. 8, 1982

[54] HELMET VISOR

[76] Inventor: William P. Bay, Rte. 1, Box 53, Ormand Beach, Fla. 32974

[21] Appl. No.: 215,228

[22] Filed: Dec. 11, 1980

[51] Int. Cl.³ .......................... A61F 9/04; A42B 3/02
[52] U.S. Cl. ........................................................ 2/10
[58] Field of Search .................... 2/10, 5, 6, 422, 423, 2/424, 185 R, 199; 24/208 A

[56] References Cited

U.S. PATENT DOCUMENTS

| 3,577,565 | 5/1971 | Feldmann et al. | 2/10 |
| 4,067,065 | 1/1978 | Slosek | 2/10 |
| 4,097,930 | 7/1978 | Bay | 2/10 |

FOREIGN PATENT DOCUMENTS

| 1421772 | 1/1976 | United Kingdom | 2/10 |

Primary Examiner—Peter P. Nerbun
Attorney, Agent, or Firm—William M. Hobby, III

[57] ABSTRACT

A visor apparatus for attachment to a helmet having snap portions thereon. The visor has a visor support portion and a visor bill portions integral therewith and protruding from the support portion. The visor support portion is curved to fit adjacent the helmet and has a plurality of generally U-shaped slots formed therein to form a plurality of resilient tabs. Each resilient tab has a snap portion attached thereto to thereby allow resilience to each mounted snap portion. Each snap portion may be reinforced by having a greater thickness than in the visor bill and each snap mounted therein may be mounted in an elongated slot. The visor support portion has a pair of end snaps mounted in horizontally elongated slots for adjustment to the helmet.

9 Claims, 8 Drawing Figures

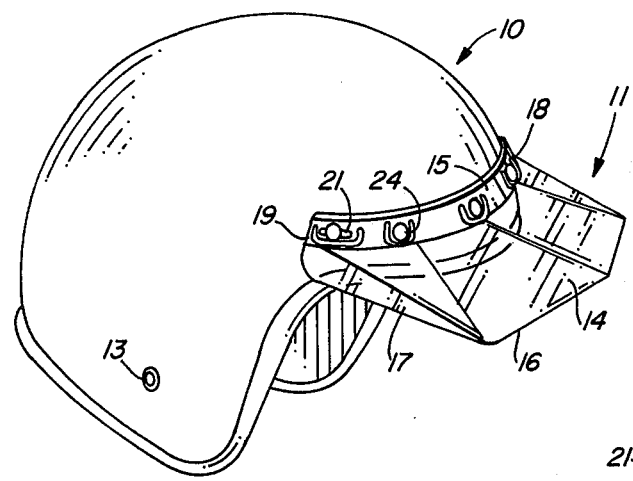
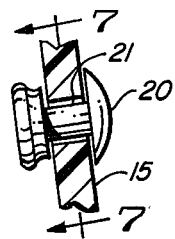
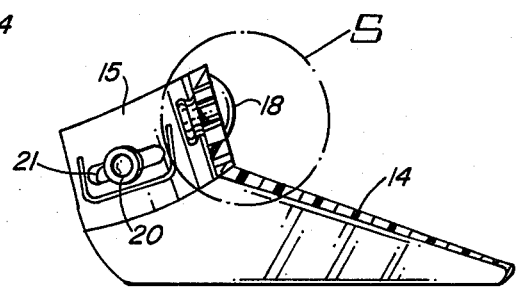
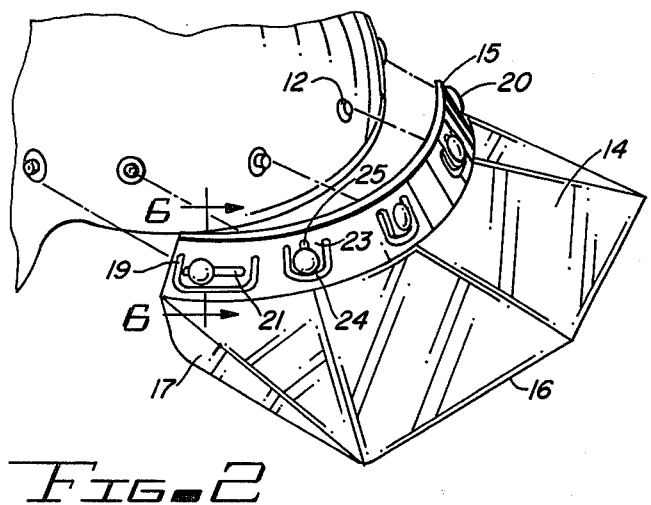
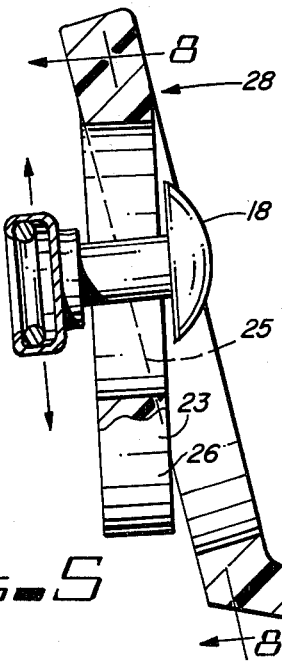
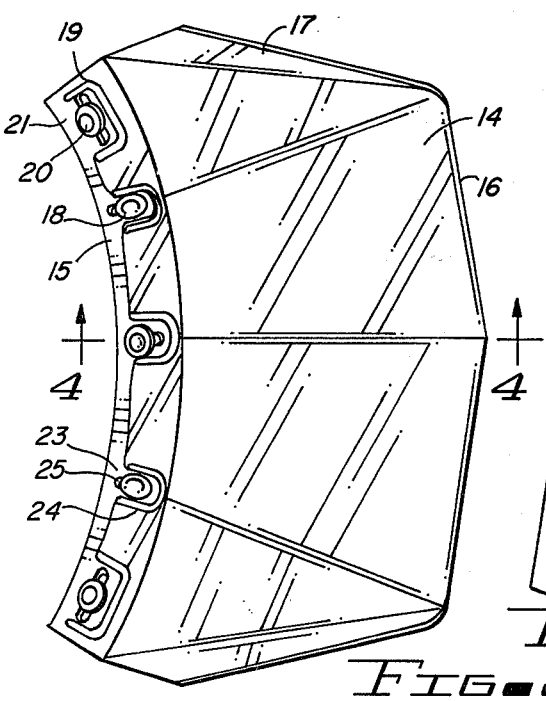
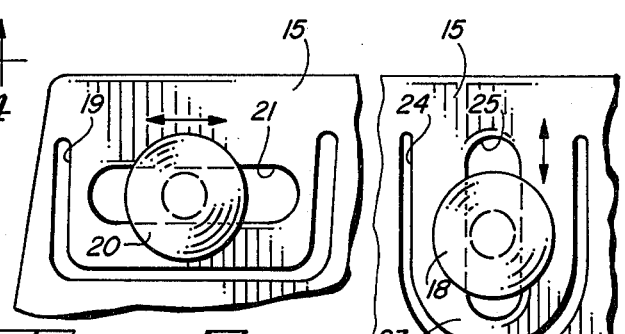

HELMET VISOR

BACKGROUND OF THE INVENTION

This invention relates to helmet visors and especially to a helmet visor for a rigid helmet such as used by motorcycle riders.

In the past, a wide variety of visors and visor and shield combinations have been produced for helmets and have a support or attachment band having three or five female snap portions mounted thereto and curved to fit on the helmet, which may have three, five, or more male snap portions. A supporting band typically has a shield or bill protruding therefrom and formed integral with a supporting band. The bill may have another band around its edge having snap fastener portions attached thereto for attaching a shield to the visor. Combined shields and visors for attachment to helmets may be seen in my prior U.S. Pat. No. 4,117,553, for Helmet Shield and Visor Apparatus; No. 4,097,930, for Helmet Shield Apparatus; and U.S. Pat. No. 254,638, for Combined Helmet Shield and Visor. One of the problems and disadvantages with a helmet visor is the impingement of air upon the visor when a motorcycle rider is moving at sufficient speed, which exerts a lifting force on the visor and helmet, which tends to lift the helmet upwards and frequently exerts sufficient force to break the rigid snaps to loosen the visor from the helmet. This problem is countered with the use of additional snaps and also more rigid snaps to prevent the visor from snapping loose. In addition, it is customary for motorcycle riders to duck their heads slightly or to turn their heads to compensate for the variable forces created by the visor and against the visor. The stiffer snaps on the visors make it difficult to attach the visor to the helmet since the snaps are attached to a fairly rigid support band on the visor, and the additional snaps make it difficult to adjust for variations in helmet snap portion positions.

One method for reducing wind forces applied to the visor is shown in U.S. Pat. No. 3,927,421, for Helmet Visor, having spoiler slots formed therein, along with wind deflector surfaces to reduce the pressure differential between one side of the visor and the other, and to reduce the pressure applied against the surface by the movement of air thereagainst.

The present invention deals with a visor designed to overcome the prior art problems of visors breaking loose as a result of the forces created by the air flow adjacent the visor, and to also ease the attachment of the visor to the helmet, and to absorb blows when the visor is hit by branches, mud, rider's gloves, or the like. The present visor also allows the wearer to pivot the visor up or down to reduce the incidence of visor angle relative to the wind stream or sun.

SUMMARY OF THE INVENTION

A visor for attachment to a helmet of the type having snap portions thereon has a visor support portion curved to fit adjacent to the helmet and a visor bill portion integral with the visor support portion and protruding therefrom. The visor support portion has a plurality fo generally U-shaped slots formed therein to thereby form resilient tabs thereon. Each U-shaped slot has a snap portion attached thereto to allow a resiliency to each mounted snap portion when attached to a helmet snap portion. The tabs formed by the U-shaped slots may be reinforced by being formed with a thicker cross section. Each tab formed in the visor support portion has an elongated vertical slot formed therein in which the snap portion is mounted through to allow the snap portion slide in a vertical direction for ease in attachment to a helmet and to provide additional resilience to the visor in a vertical direction and for making small adjustments to the angle of the visor. The end snaps on the visor are mounted in horizontal slots for adjustment to different helmets. The visor bill portion is made having a center cross section to allow additional flexibility in the bill portion, rather than to the support portion of the visor.

BRIEF DESCRIPTION OF THE DRAWINGS

Other objects, features and advantages of the present invention will be apparent from the written description and the drawings in which:

FIG. 1 is a perspective view of a helmet having a preferred embodiment of the present invention attached thereto;

FIG. 2 is a fragmented exploded view of the helmet and visor of FIG. 1;

FIG. 3 is a bottom elevation of the visor in accordance with FIGS. 1 and 2;

FIG. 4 is a sectional view taken on the line 4—4 of FIG. 3;

FIG. 5 is a sectional view taken on the circle 5 of FIG. 4;

FIG. 6 is a sectional view taken on the line 6—6 of FIG. 2;

FIG. 7 is a sectional view taken on the line 7—7 of FIG. 6; and

FIG. 8 is a sectional view taken on the line 8—8 of FIG. 5.

DESCRIPTION OF THE PREFERRED EMBODIMENT

Referring to the drawings, a helmet 10 has a visor 11 in accordance with the present invention attached thereto in FIG. 1. The helmet 10 is a typical motorcycle helmet having five male snap portions 12 for attaching a shield or visor. The helmet 10 also has a pair of snap portions 13 which can attach to the bottom portions of a shield. The visor 11 has a bill or shield portion 14 protruding from and integral with a support or attachment band portion 15. The band 14 may have a reinforced edge 16 and side shield portions 17. The attachment and support portion 15 has a plurality of center snaps 18 and a pair of end snaps 20. The end snaps 20 are mounted in horizontal slots 21 so that the snap portions may be slid to coincide with male snap portions 22 on the helmet 10 and are mounted on tabs formed by U-shaped slots 19. The plurality of center snap portions 18 are each mounted on tabs 23 formed in the arcuate visor support portion 15 by U-shaped slots 24. The female snap portions 18 are mounted in vertically extending elongated slots 25 to allow adjustment in the attaching of the snap portions to the male snap portions 12 on the helmet 10. The tabs 23 formed by the U-shaped slots 24 may have a thicker cross section as indicated in FIG. 5, which is formed in the injection mold, while the bill portion 14 may have thinner cross section 27 than the cross section 26 of the tab 23. The cross section thickness 27 of the bill 14 in fact, is less than the support band 15 and of the normal thickness provided for in helmet visors to give greater flexibility to the bill portion relative to the support portion. The thinness is also made possible by the design of the support portion 15 having the tabs 23 formed therein. In operation, the male snap portions 24 can be easily attached to the helmet 10 snap portions 12 because of the resilience of the tabs 23. Once attached to the helmet 10, air currents and pressure differentials will not normally snap the visor 11 from the helmet because the visor tends to shift slightly or give under the resilience of the tabs 23 having the snaps attached thereto, which are in turn attached to the helmet 10. This resilience plus the added resilience of the bill portion 14 and by the slots 25 allows movement of the snaps in a vertical direction. The fasteners 20 are attached to the fastener portions 22 and acting as a hinge during slight movement resulting from the resilience of the visor.

That is, under air currents and pressure differentials, the tabs 23 formed by the U-slots 24 are supported or hinged along their top portions 28 with a thickened cross section and of a material giving a resilience to allow the tabs to bend as illustrated in FIG. 5, and then to return to its original position after a sudden increase in air pressure against the visor is reduced. Similar, the visor is better able to absorb blows from tree branches, mud, or the like. The visor also allows snap portions 18 to be made with less holding force, thereby being easy to snap to the snap portions 12 and may be made of other materials to reduce the cost of the snaps.

It should be clear at this point that a new visor and visor attachment means has been provided for attaching a visor to a rigid helmet. The visor allows a wearer to make small adjustments to pivot the visor up or down to reduce the incidence of visor angle relative to the wind stream or other conditions. However, the present is not be be construed as limited to the form shown, which is to be considered illustrative, rather than restrictive.

I claim:

1. A visor for attachment to a helmet having snap portions thereon comprising in combination:
    a visor support portion curved to fit adjacent said helmet;
    a visor bill portion integral with said visor support portion and protruding therefrom;
    said visor support portion having a plurality of generally U-shaped elongated apertures formed therein forming a plurality of resilient tabs, each tab formed by said U-shaped elongated apertures having a snap portion attached thereto resiliently mounting each said snap portion to said visor support portion when attached to a helmet, thereby giving said visor resilience relative to said helmet.

2. A visor in accordance with claim 1, in which said tabs formed by said U-shaped elongated apertures in said visor support portion have a cross section thicker than said visor bill portion.

3. A visor in accordance with claim 2, in which said resilient tabs formed by said U-shaped elongated apertures in said visor support portion have elongated apertures therein with said snap portions attached to said elongated apertures thereby allowing movement of said snap portions along said elongated apertures.

4. A visor in accordance with claim 3, in which at least one said resilient tab elongated apertures extend in a generally vertical direction when attached to a helmet.

5. A visor in accordance with claim 4, in which said visor support portion is reinforced with a thickened cross section relative to said visor bill portion.

6. A visor in accordance with claim 4, in which said visor support portion has a snap portion on each end portion thereof attached in an elongated aperture extending in a generally horizontal direction when said visor is attached to a helmet.

7. A visor in accordance with claim 1, formed of a polymer material having metal snap portions attached to said tabs.

8. A visor in accordance with claim 7, in which at least one said tab has a vertically extending elongated aperture and one said snap portion is attached through said elongated aperture.

9. A visor in accordance with claim 7, in which said visor attachment portion has a snap portion mounted on each end of the arcuate surface in a horizontally extending aperture.

* * * * *